United States Patent [19]
Fernández-Gadea et al.

[11] Patent Number: 5,773,433
[45] Date of Patent: Jun. 30, 1998

[54] SUBSTITUTED TETRACYCLIC OXAZEPINE AND THIAZEPINE DERIVATIVES

[75] Inventors: Francisco Javier Fernández-Gadea, Toledo, Spain; Victor Karel Sipido, Merksem, Belgium; José Ignacio Andrés-Gil, Madrid, Spain; Theo Frans Meert, Rumst, Belgium

[73] Assignee: Janssen Pharmaceutica, N.V., Beerse, Belgium

[21] Appl. No.: 817,989

[22] PCT Filed: Oct. 25, 1995

[86] PCT No.: PCT/EP95/04197

§ 371 Date: Apr. 25, 1997

§ 102(e) Date: Apr. 25, 1997

[87] PCT Pub. No.: WO96/14321

PCT Pub. Date: May 17, 1996

[30] Foreign Application Priority Data

Nov. 2, 1994 [EP] European Pat. Off. .............. 94203177

[51] Int. Cl.⁶ ..................... C07D 498/04; C07D 513/04; A61K 31/55
[52] U.S. Cl. ........................ 514/211; 540/546; 540/547
[58] Field of Search .................................. 540/546, 547; 514/211

[56] References Cited

U.S. PATENT DOCUMENTS 4,039,558   8/1977   van der Burg et al. ......... 260/326.5 B

FOREIGN PATENT DOCUMENTS

A 0 421 823 A2   4/1991   European Pat. Off. .

OTHER PUBLICATIONS

Obara et al., Chemical Abstracts, vol. 126 No. 4, p. 584, (abstract for WO 9633983). Jan. 27, 1997.

Primary Examiner—Emily Bernhardt
Assistant Examiner—Ann M. Kessinger
Attorney, Agent, or Firm—Ellen Ciambrone Coletti

[57] ABSTRACT

This invention concerns the compounds of formula (I), the pharmaceutically acceptable salts and stereoisomeric forms thereof, and also the N-oxide forms thereof.

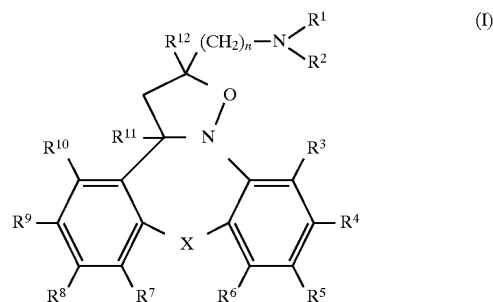

wherein: $R^1$ and $R^2$ each independently are hydrogen; $C_{1-6}$alkyl; $C_{1-6}$alkylcarbonyl; trihalomethylcarbonyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl; or $R^1$ and $R^2$ taken together with the nitrogen atom to which they are attached may form a morpholinyl ring or an optionally substituted heterocycle; $R^3$ to $R^{10}$ each independently are hydrogen, halo, cyano, hydroxy, trifluoromethyl, trifluoromethoxy, carboxyl, nitro, amino, mono- or di($C_{1-6}$alkyl)amino, $C_{1-6}$alkylcarbonylamino, aminosulfonyl, mono- or di($C_{1-6}$alkyl)-aminosulfonyl, $C_{1-6}$alkyl, $C_{1-6}$alkyloxy, $C_{1-6}$alkylcarbonyl, $C_{1-6}$alkyloxycarbonyl; $R^{11}$ is hydrogen, $C_{1-6}$alkyl, or trifluoromethyl; $R^{12}$ is hydrogen, $C_{1-6}$alkyl, cyano, or trifluoromethyl; n is zero to 6; and X is O, S, S(=O) or S(=O)$_2$. The compounds of formula (I) may be used as therapeutic agents in the treatment or the prevention of CNS disorders, cardiovascular disorders or gastrointestinal disorders.

21 Claims, No Drawings

SUBSTITUTED TETRACYCLIC OXAZEPINE AND THIAZEPINE DERIVATIVES

CROSS-REFERENCE TO RELATED APPLICATIONS

This application is the national stage of application No. PCT/EP 95/04197, filed on Oct. 25, 1995, which application claims priority from EP 94.203.177.4, filed on Nov. 2, 1994.

This invention concerns substituted tetracyclic oxazepine and thiazepine derivatives having antipsychotic, cardiovascular and gastrokinetic activity and their preparations; it further relates to compositions comprising them, as well as their use as a medicine.

Compounds of similar structure are described in U.S. Pat. No. 4,039,558 which discloses pyrrolidinodibenzo-azepine, -oxazepine, -thiazepine and -diazepine derivatives, having antihistamine, sedative and antidepressant properties. EP-A-0,421,823 describes similar dibenzopyrazino- or benzopyrido-pyrazino-azepine derivatives having anti-allergic and anti-asthmatic activities. The present compounds differ therefrom by the presence of an isoxazolidine ring, and by their pharmacological properties.

This invention concerns compounds of formula

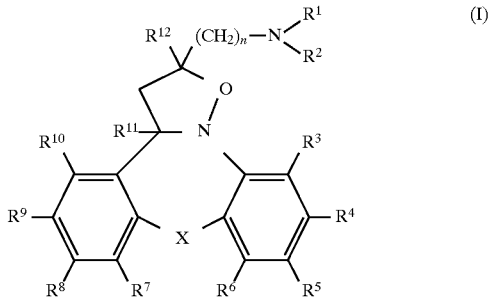

the pharmaceutically acceptable acid or base addition salts and the stereochemically isomeric forms thereof, and also the N-oxide forms thereof, wherein: $R^1$ and $R^2$ each independently are hydrogen; $C_{1-6}$alkyl; $C_{1-6}$alkylcarbonyl; trihalomethylcarbonyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl; or $R^1$ and $R^2$ taken together with the nitrogen atom to which they are attached may form a morpholinyl ring or a radical of formula:

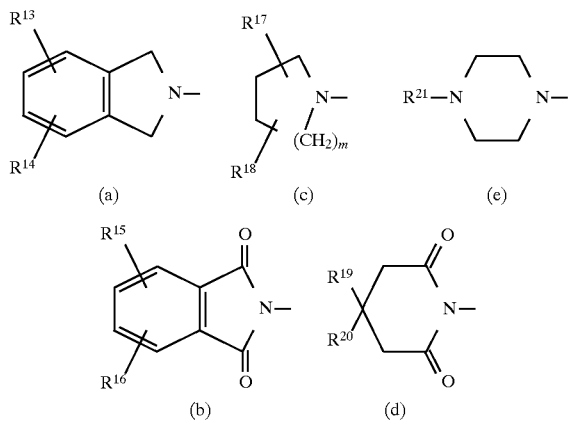

wherein:
$R^{13}$, $R^{14}$, $R^{15}$ and $R^{16}$ each independently are hydrogen, halo, trifluoromethyl, or $C_{1-6}$alkyl;

m is 1,2,or 3;
$R^{17}$, $R^{18}$, $R^{19}$ and $R^{20}$ each independently are hydrogen or $C_{1-6}$alkyl; or
$R^{19}$ and $R^{20}$ taken together may form a bivalent radical $C_{4-5}$alkanediyl;
$R^{21}$ is hydrogen; $C_{1-6}$alkyl; $C_{1-6}$alkylcarbonyl; trihalomethylcarbonyl;
$C_{1-6}$alkyloxycarbonyl; aryl; di(aryl)methyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl;
$R^3$, $R^4$, $R^5$, $R^6$, $R^7$, $R^8$, $R^9$ and $R^{10}$ each independently are hydrogen, halo, cyano, hydroxy, trifluoromethyl, trifluoromethoxy, carboxyl, nitro, amino, mono- or di($C_{1-6}$alkyl)amino, $C_{1-6}$alkylcarbonylamino, aminosulfonyl, mono- or di($C_{1-6}$alkyl)-aminosulfonyl, $C_{1-6}$alkyl, $C_{1-6}$alkyloxy, $C_{1-6}$alkylcarbonyl, $C_{1-6}$alkyloxycarbonyl;
$R^{11}$ is hydrogen, $C_{1-6}$alkyl or trifluoromethyl;
$R^{12}$ is hydrogen, Cl 6alkyl, cyano or trifluoromethyl;
n is zero, 1, 2, 3, 4, 5, or 6;
X is O, S, S(=O) or S(=O)$_2$;
aryl is phenyl; or phenyl substituted with 1, 2 or 3 substituents selected from halo, hydroxy, $C_{1-6}$alkyl and trifluoromethyl.

In the foregoing definitions $C_{1-6}$alkyl defines straight and branch chained saturated hydrocarbon radicals having from 1 to 6 carbon atoms such as, for example, methyl, ethyl, propyl, butyl, 1-methylpropyl, 1,1-dimethylethyl, pentyl, hexyl; $C_{4-5}$alkanediyl defines bivalent straight and branch chained saturated hydrocarbon radicals having from 4 to 5 carbon atoms such as, for example, 1,4-butanediyl, 1,5-pentanediyl; halo is generic to fluoro, chloro, bromo and iodo.

The pharmaceutically acceptable acid addition salts as mentioned hereinabove are meant to comprise the therapeutically active non-toxic acid addition salt forms which the compounds of formula (I) are able to form. Said salts can be obtained by treating the base form of the compounds of formula (I) with appropriate acids such as inorganic acids, for example, hydrohalic acid, e.g. hydrochloric or hydrobromic, sulfuric, nitric, phosphoric and the like acids; or organic acids, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluene-sulfonic, cyclamic, salicylic, p-aminosalicylic, pamoic and the like acids.

The compounds of formula (I) containing acidic protons may also be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted into the free forms by treatment with an appropriate base or acid.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I) are meant to comprise those compounds of formula (I) wherein one or several nitrogen atoms are oxidized to the so-called N-oxide, particularly those N-oxides wherein the nitrogen bearing the $R^1$ and $R^2$ substituents is N-oxidized.

The term "stereochemically isomeric forms" as used hereinbefore and hereinafter defines all the possible isomeric forms in which the compounds of formula (I) may occur. Unless otherwise mentioned or indicated, the chemical designation of compounds denotes the mixture, in particular the racemic mixture, of all possible stereochemically isomeric forms, said mixtures containing all diastereomers and enantiomers of the basic molecular structure. Stereochemically isomeric forms of the compounds of formula (I) and mixtures of such forms are obviously intended to be encompassed by formula (I).

The numbering of the tetracyclic ring-system present in the compounds of formula (I), as defined by Chemical Abstracts nomenclature is shown in formula (I).

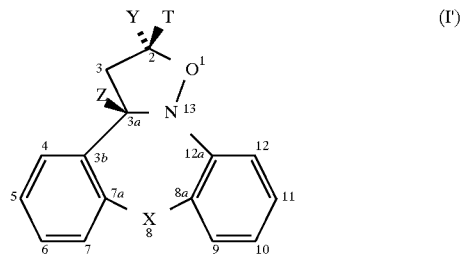

The compounds of formula (I) occur as "cis" and "trans" isomers. Said terms refer to the position of the substituents on the isoxazolidine ring and are in accordance with Chemical Abstracts nomenclature. The nomenclature is unusual in that carbon atom 3b, being part of a cyclic system, is not considered as a relevant substituent of carbon atom 3a. When establishing the configuration, the substituent on carbon atom 3a (i.e. "Z") and the substituent with the highest priority on carbon atom 2 (i.e. either "T" or "Y") are considered. When "Z" and the substituent with the highest priority on carbon atom 2 are on the same side of the mean plane determined by the isoxazolidine ring then the configuration is designated "cis", if not, the configuration is designated "trans".

The compounds of formula (I) have at least two asymmetric centers, namely carbon atom 3a bearing the substituent $R^{11}$ and carbon atom 2 bearing the substituent $R^{12}$. Said asymmetric centers and any other asymmetric center which may be present, are indicated by the descriptors R and S.

Whenever used hereinafter, the term compounds of formula (I) is meant to also include the pharmaceutically acceptable acid addition salts, base addition salts and all stereoisomeric forms and also the N-oxide forms.

Particular groups of compounds of formula (I) are those wherein one or more of the following restrictions apply:

a) $R^1$ and $R^2$ each independently are hydrogen, $C_{1-6}$alkyl, trihalomethylcarbonyl, $C_{1-6}$alkyl substituted with carboxyl or $C_{1-6}$alkyloxycarbonyl, or $R^1$ and $R^2$ taken together with the nitrogen atom to which they are attached form a morpholinyl ring or a radical of formula (b), (c), (d), (e);

b) $R^{15}$ and $R^{16}$ are hydrogen;

c) $R^{17}$ and $R^{18}$ are hydrogen and m is 1 or 2;

d) $R^{19}$ and $R^{20}$ are taken together to form a bivalent $C_{4-5}$alkanediyl radical;

e) $R^{21}$ is hydrogen, $C_{1-6}$alkyl, di(aryl)methyl, $C_{1-6}$alkyloxycarbonyl, trihalomethylcarbonyl, $C_{1-6}$alkyl substituted with hydroxy, carboxyl, $C_{1-6}$alkyloxycarbonyl;

f) $R^3$, $R^4$, $R^5$, $R^6$ each independently are hydrogen, halo, trifluoromethyl, $C_{1-6}$alkyloxycarbonyl, $C_{1-6}$alkylaminosulfonyl, carboxyl;

g) $R^7$, $R^8$, $R^9$, $R^{10}$ each independently are hydrogen, halo, trifluoromethyl, $C_{1-6}$alkyloxycarbonyl, $C_{1-6}$alkylaminosulfonyl, carboxyl;

h) $R^{11}$ and $R^{12}$ are hydrogen;

i) X is O, S or S(=O).

Interesting compounds are those compounds of formula (I) or subgroups as defined above, wherein $R^3$, $R^5$, $R^6$, $R^7$, $R^{10}$, $R^{11}$ and $R^{12}$ are hydrogen; and in particular, $R^4$, $R^8$ and $R^9$ each independently are selected from $C_{1-6}$alkyloxycarbonyl and carboxyl, preferably $R^4$, $R^8$ and $R^9$ each independently are selected from hydrogen, halo, trifluoromethyl and $C_{1-6}$alkylaminosulfonyl.

Also interesting compounds are those compounds of formula (I) or subgroups as defined above, wherein n is 1, 2 or 3 and X is O.

Further interesting compounds are those compounds of formula (I) or subgroups as defined above, wherein n is 1 and X is S or S(=O).

More interesting compounds are those interesting compounds in which $R^1$ and $R^2$ each independently are selected from hydrogen, methyl, $C_{1-6}$alkyl substituted with carboxyl or $C_{1-6}$alkyloxycarbonyl; or $R^1$ and $R^2$ taken together with the nitrogen atom to which they are attached from a morpholinyl ring or a radical of formula (b), (c) or (e).

Preferred compounds are those compounds of formula (I) wherein X is O; n is 1, 2 or 3; $R^1$ and $R^2$ are both methyl, or together with the nitrogen atom to which they are attached form a radical of formula (b) in which $R^{15}$ and $R^{16}$ are both hydrogen, or a radical of formula (e) in which $R^{21}$ is hydrogen, $C_{1-6}$alkyl or trifluoromethylcarbonyl; $R^4$ and $R^9$ each independently are selected from hydrogen, halo, trifluoromethyl, $C_{1-6}$alkyl-aminosulfonyl; $R^3$, $R^5$ to $R^8$ and $R^{10}$ to $R^{12}$ being hydrogen.

The most preferred compounds are:

cis-2-[(dimethylamino)methyl]-3,3a-dihydro-N-methyl-2H-dibenz[b,f]isoxazolo[2,3-d]-[1,4]oxazepine-11-sulfonamide;

cis-11-chloro-3,3a-dihydro-2-(1-piperazinylmethyl)-2H-dibenz[b,f]isoxazolo[2,3-d]-[1,4]oxazepine;

cis-2-[[3,3a-dihydro-11-(trifluoromethyl)-2H-dibenz[b,f]isoxazolo[2,3-d][1,4]oxazepin-2-yl]methyl]-1H-isoindole-1,3-(2H)-dione; and cis-11-chloro-3,3a-dihydro-N,N-dimethyl-2H-dibenz[b,f]isoxazolo[2,3-d][1,4]-oxazepine-2-propanamine;

the stereochemically isomeric forms and pharmaceutically acceptable acid addition salts thereof, and also their N-oxide forms.

Interestingly, the compounds of formula (I) are fairly simple to synthesise. In general, they may be prepared by a 1,3-dipolar cycloaddition of a dienophile of formula (III) and an intermediate of formula (II). In the intermediates (II) and (III) and in any other intermediate mentioned hereinunder, $R^1$ to $R^{12}$, X and n are as defined hereinabove, unless otherwise indicated. Said 1,3-dipolar cycloaddition may conveniently be carried out by mixing the reactants, optionally in a reaction-inert solvent such as, for example, an aromatic solvent, e.g. toluene; an ether, e.g. tetrahydrofuran, or a mixture of such solvents. Stirring and elevated temperatures, or increased pressure may enhance the rate of the reaction. The reaction of intermediate (II) with intermediate (III) in practice is regioselective yielding compounds of formula (I).

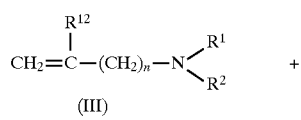

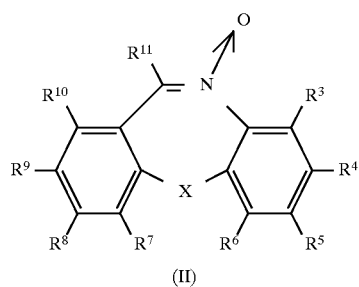

In this and the following preparations, the reaction products may be isolated from the reaction medium and, if necessary, further purified according to methodologies generally known in the art such as, for example, extraction, crystallization, trituration and chromatography.

The compounds of formula (I) may also be converted into each other following art-known transformations. For example, a) a compound of formula (I), wherein $R^1$ and $R^2$ taken together with the nitrogen atom to which they are attached form a radical of formula (b) may be converted into the corresponding primary amine by treatment with hydrazine or aqueous alkali;

b) a compound of formula (I), wherein $R^1$ or $R^2$ is trifluoromethylcarbonyl, may be converted into the corresponding primary or secondary amine by hydrolysis with aqueous alkali;

c) a compound of formula (I), wherein $R^1$ or $R^2$ is $C_{1-6}$alkyl substituted with $C_{1-6}$alkylcarbonyloxy may be hydrolyzed into a compound of formula (I) wherein $R^1$ or $R^2$ is $C_{1-6}$alkyl substituted with hydroxy;

d) a compound of formula (I), wherein $R^1$ and $R^2$ are both hydrogen may be mono- or di-N-alkylated to the corresponding amine form;

e) a compound of formula (I), wherein $R^1$ and $R^2$ are both hydrogen may be N-acylated to the corresponding amide;

f) a compound of formula (I), containing a $C_{1-6}$alkyloxycarbonyl group may be hydrolyzed to the corresponding carboxylic acid.

The compounds of formula (I) wherein X is other than S, may be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)-oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Intermediates of formula (II) wherein X is O, S(=O) or S(=O)$_2$, said intermediates are represented by formula (II-a), may be prepared by the oxidation of an intermediate of formula (IV) with a suitable oxidizing agent such as, for example, 2-benzenesulfonyl-3-phenyl-oxaziridine, hydrogen peroxide, t-butyl hydroxyperoxide, or metachloroperbenzoic acid.

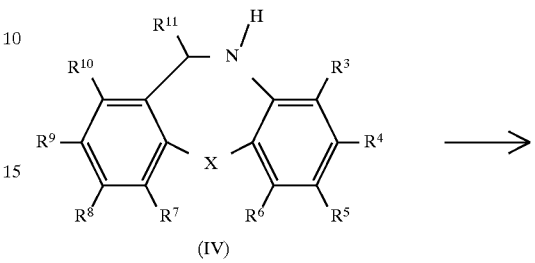

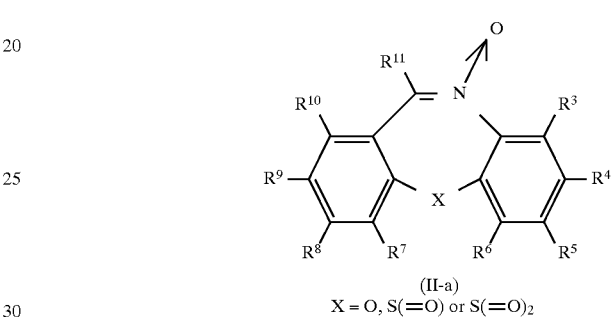

Said oxidation is performed in a reaction-inert solvent at temperatures ranging between −20° C. and 50° C., preferably between 0° C. and room temperature. Suitable solvents are, for example, water; chlorinated hydrocarbons, e.g. chloroform; aromatic hydrocarbons, e.g. toluene; alcohols, e.g. methanol; ketones, e.g. 4-methyl-2-pentanone; or a mixture of such solvents. When using peroxide oxidants, the reaction rate may be enhanced by using metallic catalysts such as, for example, Na$_2$WO$_4$, VO(acetylacetonate)$_2$, Ti(OBu)$_4$, and MoO$_2$(acetylacetonate)$_2$, optionally under a reaction inert atmosphere such as, for example, argon.

Alternatively, intermediates of formula (II) wherein $R^{11}$ is hydrogen and $R^3$ to $R^{10}$ are defined as hereinabove but other than nitro, said intermediates are represented by formula (II-b), may be prepared by reducing the nitro group of an intermediate of formula (V) in the presence of water and a suitable reducing agent such as, for example, zinc or iron; subsequently followed by an in situ intramolecular cyclization in the presence of a weak acid such as, for example, ammoniumchloride or acetic acid. Said reductive cyclization is performed in a reaction-inert solvent such as, for example, 1,4-dioxane. Stirring and elevated temperatures may enhance the rate of the reaction. In intermediate (V), $R^3$ to $R^{10}$ are defined as in intermediates of formula (II-b).

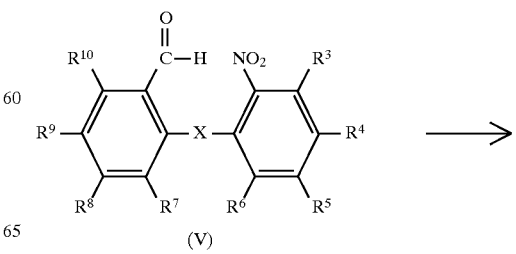

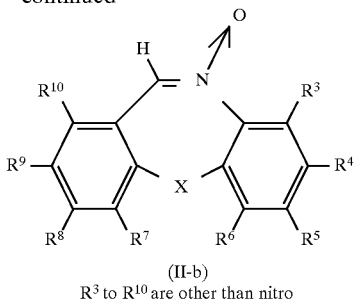

(II-b)
R³ to R¹⁰ are other than nitro

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The pharmacological activity of the subject compounds is elucidated by one or more of the following tests; in vitro 5-HT₂ receptor binding tests; the combined apomorphine, tryptamine and norepinephrine test on rats which is described in Arch. Int. Pharmacodyn., 227, 238–253 (1977); the "mCPP Test on Rats"; and the "Elevated and Illuminated Plus Maze Test on Rats". The latter two tests are both described hereinafter. Additionally, the present compounds show interesting pharmacological activity in the "Tail Suspension Test", and also in the "LSD Drug Discrimination Test" which is described in Drug Dev. Res. 18, 119–144 (1989). Another interesting property of the compounds of formula (I) is that they suppress amphetamine-induced stereotypical behaviour in rats.

In view of their pharmacological properties, the compounds of formula (I) are useful as therapeutic agents in the treatment or the prevention of central nervous system disorders like anxiety, depression and mild depression, bipolar disorders, sleep- and sexual disorders, psychosis, borderline psychosis, schizophrenia, migraine, personality disorders or obsessive-compulsive disorders, social phobias or panic attacks, organic mental disorders, mental disorders in children, aggression, memory disorders and attitude disorders in older people, addiction, obesity, bulimia and similar disorders. In particular, the present compounds may be used as anxiolytics, antidepressants and as agents having the potential to overrule the addictive properties of drugs of abuse.

The compounds of formula (I) may also be used as therapeutic agents in the treatment of motoric disorders. It may be advantageous to use the present compounds in combination with classic therapeutic agents for such disorders.

The compounds of this invention may also serve as therapeutic agents in the treatment or the prevention of damage to the nervous system caused by trauma, stroke, neurodegenerative illnesses and the like; cardiovascular disorders like high blood pressure, thrombosis, stroke, and the like; and gastrointestinal disorders like dysfunction of the motility of the gastrointestinal system and the like. The present compounds may also be useful as anticonvulsive agents.

In view of the above uses of the compounds of formula (I), it follows that the present invention also provides a method of treating warm-blooded animals suffering from such diseases, said method comprising the systemic administration of a therapeutic amount of a compound of formula (I) effective in treating the above described disorders.

The present invention thus also relates to compounds of formula (I) as defined hereinabove for use as a medicine, in particular for use as a medicine to treat the above described disorders.

Those of skill in the treatment of such diseases could determine the effective therapeutic daily amount from the test results presented hereinafter. An effective therapeutic daily amount would be from about 0.001 mg/kg to about 10 mg/kg body weight, more preferably from about 0.005 mg/kg to about 1 mg/kg body weight.

For ease of administration, the subject compounds may be formulated into various pharmaceutical forms for administration purposes. To prepare the pharmaceutical compositions of this invention, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (1) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wet-table agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid or base addition salts of compounds of formula (I) due to their increased water solubility over the corresponding base or acid form, are obviously more suitable in the preparation of aqueous compositions.

In order to enhance the solubility and/or the stability of the compounds of formula (I) in pharmaceutical compositions, it can be advantageous to employ α, β, γ-cyclodextrins or their derivatives, in particular hydroxy-alkyl substituted cyclodextrins, e.g. 2-hydroxy-propyl-β-cyclodextrin. Also co-solvents such as alcohols may improve the solubility and/or the stability of the compounds of formula (I) in pharmaceutical compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate and not to limit the scope of the present invention.

EXPERIMENTAL PART

A. Preparation of the intermediates

Hereinunder, "EtOAc" means ethylacetate, "DMF" means dimethylformamide and "RT" means room temperature.

Example 1 a) A mixture of 1-(2-propenyl)piperazine (6.6 g) and ethyl 2-propenoate (11.3 ml) in ethanol (100 ml) was stirred and refluxed for 1 hour 30 minutes. The solvent was evaporated, yielding 9.6 g (80%) of ethyl 4-(2-propenyl)-1-piperazinepropanoate (interm. 1).

b) A mixture of intermediate 1 (7.5 g) in a hydrochloric acid solution (35%) (20 ml), acetic acid (20 ml) and water (10 ml) was stirred and refluxed for 4 hours. The mixture was cooled on an ice bath and NaOH (50%) was added so the mixture was at a pH of about 6 and the solvent was evaporated. The residue was treated with EtOAc, the precipitate was filtered off and the filtrate evaporated. The oily residue was dissolved in toluene and the solvent was evaporated. The residue was purified by short open column chromatography over silica gel (eluent: $CH_2Cl_2/(CH_3OH/NH_3)$ 8/2). The pure fractions were collected and evaporated, yielding 5.3g (81%) of 4-(2-propenyl)-1-piperazinepropanoic acid (interm. 2).

Example 2

A mixture of 2-hydroxybenzaldehyde (16.7 g) and $Al_2O_3/KF$ (65.5 g) in DMF was heated to 120° C. under a $N_2$ atmosphere and 4-bromo-1-fluoro-2-nitrobenzene (30 g) in DMF was added. The mixture was stirred at 120° C. for 3 hours. The precipitate was filtered off and the filtrate evaporated. The residue was purified by open column chromatography over silica gel (eluent 1: hexane/$CH_2Cl_2$/AcOEt 8/1/1; eluent 2: $CH_2Cl_2$/2-propanone 9/1) and the pure fractions were collected, yielding 26 g (59%) of 2-(4-bromo-2-nitrophenoxy)benzaldehyde (interm. 3). Analogously, 5-chloro-2-(2-nitrophenoxy)benzaldehyde (interm. 4) was prepared.

Example 3 a) 1,4-dichloro-2-nitrobenzene (31.6 g) was added to a mixture of 2,2'-dithiodi-benzaldehyde (41 g) and potassium carbonate (41.3 g) in methanol (820 ml) and the reaction mixture was stirred and refluxed for 2 hours. More 1,4-dichloro-2-nitrobenzene (31.6 g) was added and the reaction mixture was stirred and refluxed for 2 hours. Water was added and the mixture was extracted with $CH_2Cl_2$. The separated organic layer was evaporated and the residue was purified by open column chromatography over silica gel (eluent: hexane/EtOAc 97.5/2.5). The pure fractions were collected and the solvent evaporated, yielding 37 g (84%) of 2-[(4-chloro-2-nitrophenyl)thio]benzaldehyde (interm. 5).

Analogously, 2-[[2-nitro-4-(trifluoromethyl)phenyl]thio]benzaldehyde (interm. 6) was prepared.

b) A mixture of potassium peroxymonosulphate (35.6 g) in water (120 ml) was added dropwise to a mixture of intermediate 5 (8.5 g) in methanol (120 ml) cooled on an ice bath and the mixture was stirred at RT for 7 hours. The solvent was evaporated, water was added and the precipitate was filtered off. The residue was purified by flash chromatography over silica gel (eluent: $CH_2Cl_2/CH_3OH_{98/2}$). The pure fractions were collected and evaporated, yielding 4.8 g (51%) 2-[(4-chloro-2-nitrophenyl)sulfinyl]-benzaldehyde (interm. 7).

Example 4 a) $LiAlH_4$ (1M) in tetrahydrofuran (100 ml) was added dropwise to a mixture of 3-chlorodibenz[b,f][1,4]oxazepin-11(10H)-one (12.3 g) (prepared as described in Indian J. Chem. 1974, 12(3), 227–35) in 1,4-dioxane (400ml) under a $N_2$ atmosphere. The mixture was stirred, refluxed for 1 hour 30 minutes, cooled and water was added dropwise. The mixture was acidified and extracted with EtOAc. The organic layer was dried with $Na_2SO_4$, filtered off and evaporated. The residue was purified by open column chromatography over silica gel (eluent: $CH_2Cl_2$). The pure fractions were collected and evaporated, yielding 9.74 g (84%) of 3-chloro-10,11-dihydrodibenz[b,f]-[1,4]oxazepine (interm.8).

b) 3-Phenyl-2-(phenylsulfonyl)oxaziridine (36.4 g) was added to a mixture of intermediate 8 (15.4 g) in trichloromethane (700 ml) and the mixture was stirred at RT for 1 hour. The solvent was evaporated and the residue was purified by open column chromatography over silica gel (eluent: $CH_2Cl_2$). The pure fractions were collected and evaporated, yielding 8.6 g (34%) of 3-chlorodibenz[b,f][1,4]oxazepine,10-oxide (interm. 9).

Example 5

A mixture of intermediate 3 (10 g) and zinc (10.3 g) in 1,4dioxane (200 ml) and water (15 ml) was stirred at RT. Ammonium chloride (4.3 g) in water (17 ml) was added dropwise at a temperature below 25° C. and the mixture was stirred at RT for 1 hour. The precipitate was filtered off and the filtrate evaporated. The residue was treated with water and extracted with $CH_2Cl_2/CH_3OH$ 9/1. The organic layer was dried, filtered off and evaporated. The residue was purified by open column chromatography over silica gel (eluent 1: $CH_2Cl_2$/hexane/EtOAc 5/4/1; eluent 2: $CH_2Cl_2$/ 2-propanone 9/1). The pure fractions were collected and evaporated, yielding 2.2 g (24%) of 8-bromodibenz-[b,f][1,4]oxazepine,10-oxide (interm. 10).

Analogously, there were prepared:

TABLE 1

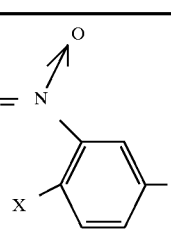

| Interm. No. | X | $R^4$ | $R^9$ |
| --- | --- | --- | --- |
| 10 | O | Br | H |
| 11 | O | H | Cl |
| 12 | O | Cl | H |
| 13 | O | $CF_3$ | H |
| 14 | O | CO—O—$CH_3$ | H |
| 15 | O | H | H |
| 16 | S | $CF_3$ | H |
| 17 | S=O | Cl | H |

B. Preparation of compounds of formula (I)

Example 6

A mixture of intermediate 15 (2.6 g) and N,N-dimethyl-2-propen-1-amine (2.9 ml) in toluene (40 ml) was stirred at 80° C. for 2 hours. The solvent was evaporated and the residue purified by column chromatography over silica gel (eluent: hexane/$CH_2Cl_2$/$CH_3OH$ 3.5/6/0.5). The pure fractions were collected and evaporated. The residue was converted into the oxalic acid salt (1:1) in $C_2H_5OH$ at RT, yielding 1 g (63%) of (±)-3,3a-dihydro-N,N-dimethyl-2H-dibenz[b,f]isoxazolo[2,3-d][1,4]-oxazepine-2-methanamine ethanedioate (1:1); mp. 179.6° C. (comp. 1).

Example 7

Following the same procedure as in example 6, but using tetrahydrofuran as a solvent, there was also prepared (±)-cis-11-chloro-3,3a-dihydro-N,N-dimethyl-2H-dibenz[b,f]-isoxazolo[2,3-d][1,4]oxazepine-2-methanamine ethanedioate(1:1); mp. 154.4° C. (comp. 2).

Example 8

A mixture of (±)-cis-1-[(11-chloro-3,3a-dihydro-2H-dibenz[b,f]isoxazolo[2,3-d][1,4]-oxazepin-2-yl)methyl]-4-(trifluoroacetyl)piperazine (7.1 g), prepared following the procedure of example 7, and potassium carbonate (4.2 g) in methanol (300 ml) and water (43 ml) was stirred at RT for 2 hours. The solvent was evaporated. The residue was treated with water, extracted with $CH_2Cl_2$ and the separated organic layer was evaporated. The residue (5.1 g) was purified by flash chromatography over silica gel (eluent: $CH_2Cl_2/CH_3OH$ 9/1, 8/2 to 7/3) and the pure fractions were collected and evaporated. The residue (4.2g) was converted into the oxalic acid salt (2:3) in $C_2H_5OH$ at room temperature, yielding 3.9 g (47%) of (±)-cis- 11-chloro-3,3a-dihydro-2-(1-piperazinylmethyl)-2H-dibenz[b,f] isoxazolo[2,3-d][1,4]oxazepine ethanedioate(2:3); mp. >250.0° C. (comp. 3).

Example 9

(±)-Methyl cis-2-[(dimethylamino)methyl]-3,3a-dihydro-2H-dibenz[b,f]isoxazolo-[2,3-d][1,4]oxazepine-11-carboxylate ethanedioate(1:1)(1.53g), prepared following the procedure in example 7, in ethanol (60 ml) was added dropwise to a mixture of sodium hydroxide (0.3 g) in water (7.5 ml) and the mixture was stirred and refluxed for 2 hours. The solvent was evaporated in vacuo and the residue was acidified with HCl (4N) to a pH of 3.6. The precipitate was filtered off, dried with $P_2O_5$ and purified by short pad column chromatography over silica gel (eluent: $CH_2Cl_2$/ ($CH_3OH/NH_3$) 7/3). The pure fractions were collected and evaporated and the residue (1 g) was treated with $CH_2Cl_2$/ $C_2H_5OH/H_2O$ 25ml/5ml/5ml. The precipitate was filtered off and dried, yielding 0.5 g (38%) of (±)-cis-2-[(dimethylamino)methyl]-3,3a-dihydro-2H-dibenz[b,f] isoxazolo[2,3-d][1,4]oxazepine-11-carboxylic acid hemihydrate; mp. 229.8° C. (comp. 4).

Example 10

A mixture of (±)-cis-2-[[3,3a-dihydro-11-(trifluoromethyl)-2H-dibenz[b,f]isoxazolo-[2,3-d][1,4] oxazepin-2-yl]methyl]-1H-isoindole-1,3(2H)-dione (2.53 g), prepared following the procedure of example 7, and hydrazine hydrate (0.28 ml) in ethanol (30 ml) was stirred at 80° C. for 5 hours. The precipitate was filtered off and the filtrate evaporated. The oily residue (3.3 g) was purified by flash chromatography over silica gel (eluent: $CH_2Cl_2$/ $CH_3OH$ 9.5/0.5). The pure fractions were collected and evaporated, and the oily residue (0.7 g) was converted into the oxalic acid salt (1:1) in $C_2H_5OH$ at RT, yielding 0.8 g (35%) of (±)-cis-3,3a-dihydro-11-(trifluoromethyl)-2H-dibenz[b,f]-isoxazolo[2,3-d][1,4]oxazepine-2-methanamine ethanedioate(1:1); mp. 250° C. (comp. 5).

Tables 2 to 5 list compounds that were prepared in a similar way as in one of the hereinabove mentioned examples.

TABLE 2

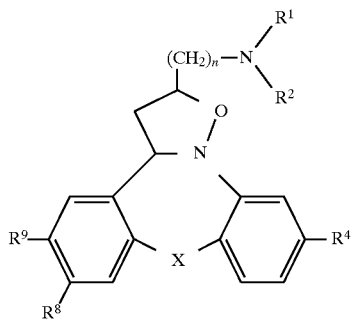

| Co. No. | Ex. No. | n | X | R¹ | R² | R⁴ | R⁸ | R⁹ | Physical data (mp. in °C.) |
|---|---|---|---|---|---|---|---|---|---|
| 1 | 6 | 1 | O | $CH_3$ | $CH_3$ | H | H | H | ±-cis/$(COOH)_2$/179.6 |
| 2 | 7 | 1 | O | $CH_3$ | $CH_3$ | Cl | H | H | ±-cis/$(COOH)_2$/154.4 |
| 4 | 9 | 1 | O | $CH_3$ | $CH_3$ | COOH | H | H | ±-cis/½$H_2O$/229.8 |
| 5 | 10 | 1 | O | H | H | $CF_3$ | H | H | ±-cis/$(COOH)_2$/250.0 |
| 6 | 9 | 1 | O | H | $CH_3$ | $CF_3$ | H | H | ±-cis/$(COOH)_2$ |
| 7 | 7 | 1 | O | $CH_3$ | $CH_3$ | F | H | H | ±-cis/$(COOH)_2$/181.3 |
| 8 | 7 | 2 | O | $CH_3$ | $CH_3$ | Cl | H | H | ±-cis/$(COOH)_2$/186.9 |
| 9 | 7 | 3 | O | $CH_3$ | $CH_3$ | Cl | H | H | ±-cis/$(COOH)_2$/164.3 |
| 10 | 7 | 6 | O | $CH_3$ | $CH_3$ | Cl | H | H | ±-cis/72.5 |
| 11 | 7 | 1 | O | $CH_3$ | $CH_3$ | H | H | Cl | ±-cis/$(COOH)_2$/181.5 |
| 12 | 7 | 1 | O | $CH_3$ | $CH_3$ | H | Cl | H | ±-cis/$(COOH)_2$/163.9 |
| 13 | 7 | 1 | O | $CH_3$ | $CH_3$ | Br | H | H | ±-cis/$(COOH)_2$/152.6 |
| 14 | 7 | 1 | O | $CH_3$ | $CH_3$ | $CF_3$ | H | H | ±-cis/$(COOH)_2$/177.8 |
| 15 | 7 | 2 | O | $CH_3$ | $CH_3$ | $CF_3$ | H | H | ±-cis/$(COOH)_2$/197.1 |
| 16 | 7 | 1 | O | $CH_3$ | $CH_3$ | $COOCH_3$ | H | H | ±-cis/$(COOH)_2$/152.4 |
| 17 | 7 | 1 | O | $CH_3$ | $CH_3$ | $SO_2NHCH_3$ | H | H | ±-cis/$(COOH)_2$/78.2 |
| 18 | 7 | 2 | S | $CH_3$ | $CH_3$ | H | H | H | ±-cis/105.8 |
| 19 | 7 | 1 | S | $CH_3$ | $CH_3$ | Cl | H | H | ±-cis/113.0 |
| 20 | 7 | 1 | S | $CH_3$ | $CH_3$ | $CF_3$ | H | H | ±-(cis + trans)/107.4 |
| 21 | 7 | 1 | SO | $CH_3$ | $CH_3$ | Cl | H | H | ±-(cis + trans)/144.7 |
| 22 | 7 | 1 | O | $CH_3$ | $CH_2$—COOH | Cl | H | H | ±-cis/$H_2O$/86.2 |
| 23 | 7 | 1 | O | $CH_3$ | $CH_2COOCH_3$ | Cl | H | H | ±-cis/$(COOH)_2$/148.1 |
| 24 | 7 | 1 | O | $CH_3$ | $(CH_2)_2COOH$ | Cl | H | H | ±-cis/½$H_2O$/57.3 |
| 25 | 7 | 1 | O | $CH_3$ | $(CH_2)_2COOC_2H_5$ | Cl | H | H | ±-cis/3/2 fumaric acid/147.3 |
| 26 | 7 | 1 | O | $CH_3$ | $(CH_2)_3COOH$ | Cl | H | H | ±-cis/$(COOH)_2$/157.2 |
| 27 | 7 | 1 | O | $CH_3$ | $(CH_2)_3COOC_2H_5$ | Cl | H | H | ±-cis/$(COOH)_2$/149.8 |
| 28 | 7 | 1 | O | $CH_3$ | $(CH_2)_4COOH$ | Cl | H | H | ±-cis/$(COOH)_2$/170.1 |
| 29 | 7 | 1 | O | $CH_3$ | $(CH_2)_4COOC_2H_5$ | Cl | H | H | ±-cis/$(COOH)_2$/155.4 |
| 30 | 9 | 1 | O | $CH_3$ | $(CH_2)_2COOH$ | H | Cl | H | ±-cis/159.5 |
| 31 | 7 | 1 | O | $CH_3$ | $(CH_2)_2COOC_2H_5$ | H | Cl | H | ±-cis |
| 32 | 7 | 1 | O | $CH_3$ | $(CH_2)_4COOH$ | H | Cl | H | ±-cis/$(COOH)_2$/148.4 |
| 33 | 7 | 1 | O | $CH_3$ | $(CH_2)_4COOC_2H_5$ | H | Cl | H | ±-cis/$(COOH)_2$/132.5 |
| 34 | 7 | 1 | O | $CH_3$ | $(CH_2)_4COOH$ | $CF_3$ | H | H | ±-cis/$(COOH)_2$ |
| 35 | 7 | 1 | O | $CH_3$ | CO—$CF_3$ | $CF_3$ | H | H | ±-cis |

TABLE 3

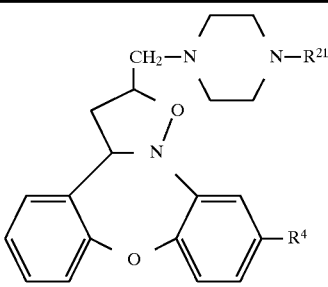

| Co. No. | Ex. No. | R⁴ | R²¹ | Physical data (mp. in °C.) |
|---|---|---|---|---|
| 3 | 8 | Cl | H | ±-cis/3/2$(COOH)_2$/>250.0 |
| 36 | 7 | Cl | $CH_3$ | ±-cis/2$(COOH)_2$/189.4 |

TABLE 3-continued

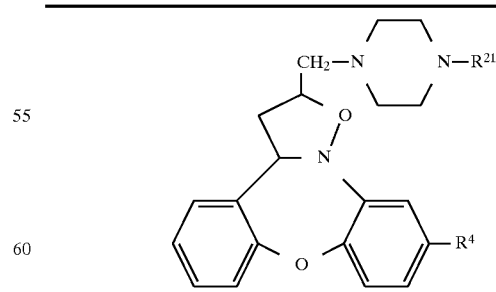

| Co. No. | Ex. No. | R⁴ | R²¹ | Physical data (mp. in °C.) |
|---|---|---|---|---|
| 37 | 7 | Cl | $(CH_2)_2$—OH | ±-cis/2$(COOH)_2$/>250.0 |
| 38 | 7 | Cl | CO—$CH_3$ | ±-cis/½$H_2O$/46.8 |

TABLE 3-continued

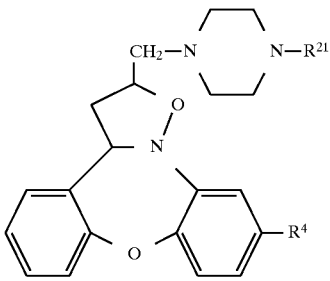

| Co. No. | Ex. No. | R⁴ | R²¹ | Physical data (mp. in °C.) |
|---|---|---|---|---|
| 39 | 7 | Cl | CO—O-t-C₄H₉ | ±-cis/124.7 |
| 40 | 7 | Cl | CO—CF₃ | ±-cis/110.9 |
| 41 | 7 | Cl | (CH₂)₂—COOH | ±-cis/H₂O/59.2 |
| 42 | 7 | Cl | (CH₂)₂—COOC₂H₅ | ±-cis/3/2(COOH)₂/266.6 |
| 43 | 7 | Cl | 3-chlorophenyl | ±-cis/154.5 |
| 44 | 7 | Cl | diphenylmethyl | ±-cis/198.4 |
| 45 | 7 | Cl | bis(4-fluorophenyl)methyl | ±-cis/107.2 |
| 46 | 7 | F | CH₃ | ±-cis/2(COOH)₂/186.2 |
| 47 | 7 | CF₃ | CH₃ | ±-cis/2(COOH)₂ |

TABLE 4

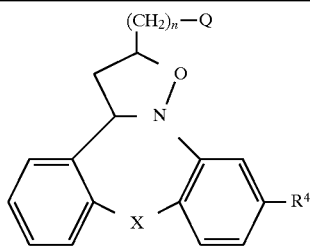

| Co. No. | Ex. No | n | X | R⁴ | Q | Physical data (mp. in °C.) |
|---|---|---|---|---|---|---|
| 48 | 7 | 1 | O | CF₃ | 7,9-dioxo-8-azaspiro[4,5]decan-8-yl | ±-cis/149.7 |
| 49 | 7 | 1 | O | CF₃ | 1-pyrrolidinyl | ±-cis/(COOH)₂/174.1 |
| 50 | 7 | 1 | O | Cl | 4-morpholinyl | ±-cis/(COOH)₂/>250.0 |
| 51 | 7 | 1 | O | CF₃ | 1,3-dihydro-1,3-dioxo-2H-isoindol-2-yl | ±-cis/165.6 |
| 52 | 7 | 2 | O | CF₃ | 1,3-dihydro-1,3-dioxo-2H-isoindol-2-yl | ±-cis/113.9 |
| 53 | 7 | 3 | O | CF₃ | 1,3-dihydro-1,3-dioxo-2H-isoindol-2-yl | ±-cis/112.2 |
| 54 | 7 | 1 | S | CF₃ | 1,3-dihydro-1,3-dioxo-2H-isoindol-2-yl | ±-(cis + trans)/135.9 |

C. Pharmacological example

Example 11: "mCPP Test on Rats"

Rats were treated with the test compound at a dose varying between 0.0025 mg/kg and 40 mg/kg body weight, at pre-test time T varying between 5 and 480 minutes, and with 1 mg/kg mCPP (metachlorophenylpiperazine), injected intravenously, 15 minutes prior to the test. After pre-test time T elapsed, treated rats were submitted to the "Open Field Test on Rats" as described in Drug Dev. Res. 18, 119–144 (1989), but using an infra-red light source instead of a Kleverlux® (12V/20W) light source. A dose at which 40% of the tested rats showed suppression of the mCPP induced effects, i.e. mCPP-antagonism, was defined as an active dose. The activity range of a test compound was measured by the ratio of the HAD (highest active dose) over the LAD (lowest active dose). The compounds with number 9 and 11 had a ratio (HAD over LAD) of 4 or more. The compounds with number 2, 3, 5–7, 10, 13, 14, 16, 18–21, 26, 28, 33, 38, 44, 48, 50 and 52 showed mCPP-antagonism at least at one tested dose.

Example 12: "Elevated and Illuminated Plus Maze Test on Rats"

The "Elevated and Illuminated Plus Maze Test on Rats" is described in Drug Dev. Res. 18, 119–144 (1989). An active dose of a test compound in said test was defined as a dose at which 40% of the tested rats explored the illuminated arms of the maze. The activity range was measured similarly as in example 11. The compounds with number 3, 8, 17, 19, 21, 40, 51, 53 and 54 had a ratio (HAD over LAD) of 4 or more. The compounds with number 1, 2, 4–6, 9–13, 16, 18, 22, 26–30, 32, 33, 36, 39, 41, 43, 44, 46, 47, 49, 50 and 52 showed activity at least at one dose in one or more of the tested rats.

D. Composition examples

"Active ingredient" (A.I.) as used throughout these examples relates to a compound of formula (I), a pharmaceutically acceptable acid addition salt, a stereochemically isomeric form thereof or a N-oxide form thereof.

Example 13: ORAL DROPS

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I.. The resulting solution was filled into suitable containers.

Example 14: ORAL SOLUTION

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5

1 of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example 15: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example 16: INJECTABLE SOLUTION 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1 l, giving a solution comprising 4 mg/ml of A.I.. The solution was sterilized by filtration and filled in sterile containers.

We claim:

1. A compound of formula (I)

the pharmaceutically acceptable acid or base addition salts and the stereochemically isomeric forms thereof, and also the N-oxide forms thereof, wherein:

$R^1$ and $R^2$ each independently are hydrogen; $C_{1-6}$alkyl; $C_{1-6}$alkylcarbonyl;

trihalomethylcarbonyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl; or $R^1$ and $R^2$ taken together with the nitrogen atom to which they are attached may form a morpholinyl ring or a radical of formula:

(a)

(b)

(c)

(d)

(e)

wherein:

$R^{13}$, $R^{14}$, $R^{15}$ and $R^{16}$ each independently are hydrogen, halo, trifluoromethyl, or $C_{1-6}$alkyl;

m is 1, 2, or 3;

$R^{17}$, $R^{18}$, $R^{19}$ and $R^{20}$ each independently are hydrogen or $C_{1-6}$alkyl; or $R^{19}$ and $R^{20}$ taken together may form a bivalent radical $C_{4-5}$alkanediyl;

$R^{21}$ is hydrogen; $C_{1-6}$alkyl; $C_{1-6}$alkylcarbonyl; trihalomethylcarbonyl;

$C_{1-6}$alkyloxycarbonyl; aryl; di(aryl)methyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl;

$R^3$, $R^4$, $R^5$, $R^6$, $R^7$, $R^8$, $R^9$ and $R^{10}$ each independently are hydrogen, halo, cyano, hydroxy, trifluoromethyl, trifluoromethoxy, carboxyl, nitro, amino, mono- or di($C_{1-6}$alkyl)amino, $C_{1-6}$alkylcarbonylamino, aminosulfonyl, mono- or di($C_{1-6}$alkyl)-aminosulfonyl, $C_{1-6}$alkyl, $C_{1-6}$alkyloxy, $C_{1-6}$alkylcarbonyl, $C_{1-6}$alkyloxycarbonyl;

$R^{11}$ is hydrogen, $C_{1-6}$alkyl or trifluoromethyl;

$R^{12}$ is hydrogen, $C_{1-6}$alkyl, cyano or trifluoromethyl;

n is zero, 1, 2, 3, 4, 5, or 6;

X is O, S, S(=O) or S(=O)$_2$;

aryl is phenyl; or phenyl substituted with 1, 2 or 3 substituents selected from halo, hydroxy, $C_{1-6}$alkyl and trifluoromethyl.

2. A compound according to claim 1, wherein $R^3$, $R^5$, $R^6$, $R^7$, $R^{10}$, $R^{11}$ and $R^{12}$ are hydrogen.

3. A compound according to claim 2, wherein n is 1, 2 or 3.

4. A compound according to claim 3, wherein $R^1$ and $R^2$ each independently are selected from hydrogen, methyl, $C_{1-6}$alkyl substituted with carboxyl or $C_{1-6}$alkyloxycarbonyl; or $R^1$ and $R^2$ taken together with the nitrogen atom to which they are attached form a morpholinyl ring or a radical of formula (b), (c) or (e).

5. A compound according to claim 1, wherein the compounds are
   cis-2-[(dimethylamino)methyl]-3,3a-dihydro-N-methyl-2H-dibenz[b,f]isoxazolo[2,3-d]-[1,4]oxazepine-11-sulfonamide;
   cis-11-chloro-3,3a-dihydro-2-(1-piperazinylmethyl)-2H-dibenz[b,f]isoxazolo[2,3-d]-[1,4]oxazepine;
   cis-2-[[3,3a-dihydro-11-(trifluoromethyl)-2H-dibenz[b,f]isoxazolo[2,3-d][1,4]oxazepin-2-yl]methyl]-1H-isoindole-1,3-(2H)-dione;
   cis-11-chloro-3,3a-dihydro-N,N-dimethyl-2H-dibenz[b,f]isoxazolo[2,3-d][1,4]oxazepine-2-propanamine;
   the stereochemically isomeric forms, pharmaceutically acceptable acid addition salts and the N-oxide forms thereof.

6. An intermediate of formula

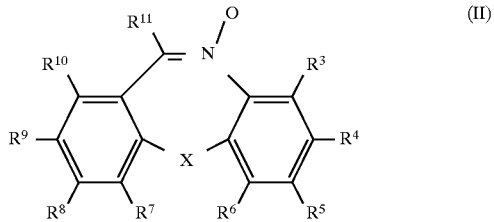

(II)

wherein $R^3$, $R^4$, $R^5$, $R^6$, $R^7$, $R^8$, $R^9$ and $R^{10}$ each independently are hydrogen, halo, cyano, hydroxy, trifluoromethyl, trifluoromethoxy, carboxyl, nitro, amino, mono- or di($C_{1-6}$alkyl)amino, $C_{1-6}$alkylcarbonylamino, aminosulfonyl, mono- or di($C_{1-6}$alkyl)-aminosulfonyl, $C_{1-6}$alkyl, $C_{1-6}$alkyloxy, $C_{1-6}$alkylcarbonyl, $C_{1-6}$alkyloxycarbonyl;
   $R^{11}$ is hydrogen, $C_{1-6}$alkyl or trifluoromethyl;
   X is O, S, S(=O) or S(=O)$_2$;
   an acid or base addition salt thereof or a stereoisomeric form thereof.

7. A composition comprising a pharmaceutically acceptable carrier and, as active ingredient, a therapeutically effective amount of a compound as defined in claim 1.

8. A composition comprising a pharmaceutically acceptable carrier and, as active ingredient, a therapeutically effective amount of a compound as defined in claim 2.

9. A composition comprising a pharmaceutically acceptable carrier and, as active ingredient, a therapeutically effective amount of a compound as defined in claim 3.

10. A composition comprising a pharmaceutically acceptable carrier and, as active ingredient, a therapeutically effective amount of a compound as defined in claim 4.

11. A composition comprising a pharmaceutically acceptable carrier and, as active ingredient, a therapeutically effective amount of a compound as defined in claim 5.

12. A method for the treatment of anxiety which comprises administering a therapeutically effective amount of a compound as defined in claim 1.

13. A method for the treatment of anxiety which comprises administering a therapeutically effective amount of a compound as defined in claim 2.

14. A method for the treatment of anxiety which comprises administering a therapeutically effective amount of a compound as defined in claim 3.

15. A method for the treatment of anxiety which comprises administering a therapeutically effective amount of a compound as defined in claim 4.

16. A method for the treatment of anxiety which comprises administering a therapeutically effective amount of a compound as defined in claim 5.

17. A method for the treatment of depression which comprises administering a therapeutically effective amount of a compound as defined in claim 1.

18. A method for the treatment of depression which comprises administering a therapeutically effective amount of a compound as defined in claim 2.

19. A method for the treatment of depression which comprises administering a therapeutically effective amount of a compound as defined in claim 3.

20. A method for the treatment of depression which comprises administering a therapeutically effective amount of a compound as defined in claim 4.

21. A method for the treatment of depression which comprises administering a therapeutically effective amount of a compound as defined in claim 5.

* * * * *